United States Patent [19]
Löffler

[11] Patent Number: 5,997,462
[45] Date of Patent: Dec. 7, 1999

[54] METHOD AND APPARATUS FOR TREATING A BLOOD VESSEL LESION

[75] Inventor: Edgar German Löffler, Kleve, Germany

[73] Assignee: Delft Instruments Intellectual Property B.V., Delft, Netherlands

[21] Appl. No.: 09/004,632

[22] Filed: Jan. 8, 1998

[51] Int. Cl.$^6$ .................................................. A61N 5/00
[52] U.S. Cl. .................................................. 600/3
[58] Field of Search .................................. 600/1–8, 159, 600/121, 124, 125; 604/533, 534, 535

[56] References Cited

U.S. PATENT DOCUMENTS

| | | | |
|---|---|---|---|
| 5,139,473 | 8/1992 | Bradshaw et al. | 600/3 |
| 5,800,333 | 9/1998 | Liprie | 600/3 |

*Primary Examiner*—Eric F. Winakur
*Attorney, Agent, or Firm*—Griffin, Butler, Whisenhunt & Szipl, LLP

[57] ABSTRACT

A method and apparatus for treating a lesion (34) of a blood vessel (33) with radiation from a radioactive source (35). A catheter (36) having at least one lumen (56) is placed into the blood vessel (33) with a distal portion (36A) near the lesion (34) and a proximal portion (49) outside of the blood vessel (33). A radiation tube (4) is at least partially placed into the catheter (36) through a lumen (56) such that a juncture (80) is formed between the proximal portion (49) of the catheter (36) and the radiation tube (4). A proximal end of the radiation tube (4) is connected to a drive device (9) for driving the radioactive source (35) through the radiation tube (4) and the catheter (36) to near the lesion (34). An axial translation device (31) is placed at the juncture (80). The axial translation device (31) has a first element (81) fixedly connected in an axial direction (A) to catheter (36) near the proximal portion (49) thereof, a second element (84) fixedly connected in the axial direction (A) to the radiation tube (4) near the juncture (80), and a third element (86) movably connected to the first element (81) and the second element (84). By moving at least one of the elements (81, 84 and 86), a relative axial translation (88) of the catheter (36) and radiation tube (4) is caused for manually positioning the radioactive source (35) near the lesion (34).

32 Claims, 3 Drawing Sheets

METHOD AND APPARATUS FOR TREATING A BLOOD VESSEL LESION

The present invention relates to an improvement in a method and apparatus for endovascular brachytherapy, especially for treating lesions, and more especially intralumenal radiotherapy and apparatus for such treatments.

BACKGROUND OF THE INVENTION

Endovascular brachytherapy is used for treatment of a wide variety of blood vessel lesions. An example thereof is the treatment of a vascular stenosis. A common treatment for a stenosis in a blood vessel is percutaneous translumenal angioplasty. The angioplasty is applicable to any blood vessel, but is very commonly carried out in connection with coronary blood vessels. Angioplasty is achieved by placing a catheter within the blood vessel near the stenosis and inflating a balloon on the catheter to cause compression of the stenosis and thus opening the occlusion. An ever present problem with such angioplasty is that of subsequent restenosis, and depending upon the particular angioplasty procedure and other factors, restenosis occurs on average in 33%, but maybe up to 45%, of all patients treated with angioplasty. The degree of restenosis varies, but restenosis can cause loss of lumen cross-sectional area such that the angioplasty is no longer successful and a further angioplasty or bypass surgery is required.

To retard or void such restenosis, in conjunction with angioplasty, a radioactive source is placed within the lesion and the lesion is radiated with certain dosages of radiation to retard or prevent restenosis.

Brachytherapy is also used to treat certain diseases, especially cancer, since the radiotherapy can be administered to very localized human body areas, as opposed to external beam radiotherapy. To achieve localized radiotherapy, a radioactive source is placed in close proximity to the tissue being treated.

In both of the above examples, the application of the radiotherapy is achieved by guiding a radioactive source through at least one radiation tube, until that source reaches the precise site of the tissue to be treated. A regimen of radiation is then administered according to a program defined for the particular tissue.

If radiation therapy, such as that exemplified above, were routinely administered to a number of patients, technicians administering the therapy would be unduly exposed to radiation hazard. To avoid such radiation hazard, apparatus has been developed for allowing the radiation source to be moved to the site of the radiotherapy while the technician is not in close proximity to the patients being treated, e.g. is not in the treatment room where the patient is being treated. Such apparatus is known in the art as remote afterloading apparatus for brachytherapy. When using such apparatus, a physician places a positioning member, e.g. a needle, canula or catheter (generically referred to as a radiation tube), at the site where the radiotherapy is to be effected. This radiation tube is attached at one end thereof to a connection head of the remote afterloading apparatus. After such positioning and connections are made, a technician can cause, e.g. from a remote location such as another room, the apparatus to drive a cable with a radioactive source attached at or near an end of the cable from a "safe" (a container for storing the radioactive source and shielding the radiation), through the remote afterloading apparatus, the radiation tube and to the site to be treated. Thus, a technician will not be in close proximity to the patients, e.g. will be in another room, while the radioactive source is out of the "safe" and while administering the therapy. Such apparatus and methods of operation are described in detail in U.S. Pat. Nos. 4,861,520; 4,881,937; 4,969,863; and 5,030,194.

Of course, it is important that the radioactive source be positioned precisely at the site of the tissue to be treated, and the afterloading apparatus usually provides means for determining the position of the source after it has passed through the afterloading apparatus and into the radiation tube. One form of such means of ensuring the correct position of the radioactive source is that of a stepping motor in the afterloading apparatus which drives a cable having the source at one end in very discrete and known steps. By use of an indexing means, the number of discrete and known steps required for the source to reach the site of treatment can be determined.

However, with afterloading machines which use a high dose rate radioactive gamma ray source, the precise position of that source in the patient cannot be determined by usual techniques of radiation, e.g. X-ray radiography or fluoroscopy device, since that high dose rate source would cause unacceptable doses of radiation to the radiation imaging system. To avoid the problem of unnecessary exposure, a "dummy" source having no radiation or very low levels of radiation is first threaded through the safe, afterloading apparatus and radiation tube to the site of the tissue to be treated. Since the dummy source does not present a radiation hazard, the exact position of that dummy source in the patient can be determined by the usual techniques of radiation, e.g. X-ray radiography and fluoroscopy device. The arrangement of such a dummy source is explained in detail in U.S. Pat. No. 5,030,194.

However, it is imperative that the technician very precisely determine the position of the radioactive source or the "dummy" (hereinafter simply "source" for conciseness purposes) and to very accurately determine the number of discrete steps of the stepping motor (or other equivalent drive apparatus) required for the particular arrangement of the radiation tube, etc., to ensure that the source has reached the precise site of tissue to be treated. This precise positioning of the source must be determined for each patient and each use of the afterloading apparatus for a patient, since the particular configurations of the flexible radiation tube, catheter, etc., can form different total lengths of travel from the afterloading apparatus to the site of radiation therapy due to the particular convolutions of the radiation tube, catheter, etc., for a specific application to a specific patient. If, for example, the radiation tube for a particular patient is configured in a substantial arc, the distance along that arc of travel for the source may well be significantly different from the travel of that source when that radiation tube is in a relatively straight configuration.

To further assist in very precise positioning of the source for irradiating a lesion, a catheter, used in the procedure, has markings thereon which are detectable by radiation, e.g. X-ray radiography or fluoroscopy device. These markings span the lesion, but those markings are not sufficiently precise for exactly positioning the source at the point of the lesion. In addition, the usual radiation tube of the afterloading apparatus is placed in a lumen of the catheter. In the case when it is placed in the catheter, it may also have such markings thereon. Accordingly, by using the stepping motor of the afterloading apparatus, the source can be placed within the markings, but it is still necessary to adjust the position of the source within those markings to the precise site of the lesion. Catheters, usually, are made of soft, flexible, supple materials which are relatively easily stretched, i.e. the length of a catheter, when inserted in the body of a patient, are, thus, not predetermined and fixed but may vary according to circumstances. The detailed description will exemplify a centering catheter with centering means in the form of one or more balloons or otherwise. It should be understood, however, that neither that centering means nor a centering catheter is required, and the present invention can be realized both with centering and with non-centering catheters and is independent of the kind of centering means used.

A centering catheter is a catheter provided with centering means for radially aligning the catheter with the blood vessel. Such centering means may comprise one or more inflatable balloons surrounding a central lumen. When the centering catheter is in a proper position, the balloon(s) are inflated. This causes the central lumen of the catheter to be centered in the lumen of the lesion such that when the source is placed within the centering catheter at the position of the lesion, it is centered within the lesion so that surrounding walls of the lesion receive equal radiation.

Heretofore, as noted above, the exact positioning of the source within the radiation tube disposed in the catheter is carried out by the technician by operating the stepping motor of the afterloading apparatus. The place (operating field) in which the procedure takes place may have a sterile area and a non-sterile area. The afterloading apparatus is not sterile and is consequently not disposed in the sterile area of the operating field. Thus, the physician in the sterile operating field must communicate with a technician operating the stepping motor for exact positioning of the source in the radiation tube and/or the catheter, and this leads to difficulties and lack of precision of source placement. Furthermore, physicians are accustomed to making minute movements of their tools happen manually. Even if the physician, who is sterile, would be allowed to touch the controls of the afterloader machine (i.e. a way could be found to make those controls sterile), then he would still be inclined to look for some other, direct and manual, control of the position of the source.

As can be seen from the above, the problem of performing the last very accurate positioning of the source for treatment of a lesion is common to all endovascular procedures, and not limited to those exemplified above, but extends to a wide variety of lesions. Accordingly, it would be of a decided advantage to the art to provide means and methods for allowing the physician to precisely and preferably manually set the position of the source in the radiation tube and catheter without having to coordinate that placement with a technician operating the controls of the afterloading machine.

SUMMARY OF THE INVENTION

It has now been discovered that a method and apparatus may be provided for precisely placing the source at the lesion for accurate radiation of the lesion. The invention is based on several primary and subsidiary discoveries.

First of all, it was discovered that an axial translation device may be placed in the sterile operating field which can cause a relative axial translation of the catheter and the radiation tube sufficient that the radioactive source is positioned precisely within the lesion. Since this axial translation device is within the sterile operating field, it can be manipulated by the physician after proximate positioning of the source by the technician. The physician, by viewing the source under radiation, can manipulate the axial translation device to very precisely position the source at the lesion in order to provide effective radiation to the lesion.

As a second primary discovery, it was found that such axial translation device can be made very simply so that the translation device is easily sterilizable for use in the operating field. The device can also be resterilized or be disposable, in view of the simple and relatively inexpensive nature of the device.

As another primary discovery, it was found that such axial translation device can be very simply and inexpensively made by providing a first element which contacts the catheter near a proximal portion thereof, a second element which contacts the radiation tube at a position thereof near the proximal portion of the catheter, and a third element which contacts the first element and the second element such as to provide axial translation between the first element and the second element.

As a subsidiary discovery, it was found that such a device can cause a relative axial translation of the catheter and radiation tube sufficient that the source is positioned precisely within the lesion.

As a further discovery, it was found that the radiation tube could be attached at a proximal end to the afterloading apparatus and the other end inserted into the catheter so as to form a juncture between the radiation tube and catheter. The axial translation device is very advantageously positioned at that juncture.

As a further subsidiary feature, it was discovered that such elements of the translation device can be simple elements, such as a lever, wheel, screw thread and gear thread. As a further subsidiary feature, it was discovered that such simple devices can very accurately position the source, particularly when the device incorporates a wheel or a rack and pinion or screw threads, although other mechanical arrangements may be used.

Thus, the present invention provides a method of treating a lesion of a blood vessel with radiation from a radioactive source. A catheter having at least one lumen is placed into the blood vessel with a distal portion near the lesion and a proximal portion outside of the blood vessel. A radiation tube is at least partially placed into the catheter through a lumen such that a juncture is formed between the proximal portion of the catheter and the radiation tube. A proximal end of the radiation tube is connected to a drive device for driving the radiation source through the radiation tube and the catheter to near the lesion. An axial translation device is placed at the juncture. The axial translation device has a first element fixedly connected in an axial direction to the catheter near the proximal portion thereof. A second element is fixedly connected in the axial direction to the radiation tube near the juncture, and a third element is movably connected to the first element and the second element. By moving at least one of the elements, a relative axial translation of the catheter and radiation tube is achieved for manually positioning the radioactive source near the lesion.

There is also provided an apparatus for treating a lesion of a blood vessel with radiation from a radioactive source. The apparatus includes a catheter having at least one lumen with a distal portion disposable within the blood vessel and preferably near the lesion and a proximal portion disposable outside of the blood vessel. A radiation tube is at least partially disposable in the catheter through a lumen such that a juncture is formed between the proximal portion of the catheter and the radiation tube. A connection connects a distal end of the radiation tube to a drive device for driving the radiation source through the radiation tube and into the catheter near the lesion. An axial translation device is disposed at the juncture. The axial translation device has a first element fixedly connected in an axial direction to the catheter near the proximal portion, a second element fixedly connected in the axial direction to the radiation tube near the juncture, and a third element movably connected to the first element and the second element. By moving at least one of the elements, a relative axial translation of the catheter and radiation tube is achieved for manually positioning the radiation source near the lesion.

Also provided is a catheter for guiding a radioactive source near a lesion of a blood vessel for treatment of the lesion. The catheter comprises an elongated catheter having at least one lumen and being extendible into a blood vessel such that a distal portion lies near the lesion and a proximal portion lies outside of the blood vessel. The lumen is capable of at least partially receiving a radiation tube for transporting a radioactive source. A juncture is formed between the proximal portion of the catheter and the radiation tube. On the proximal portion there is disposed a portion of an axial translation device. That portion comprises a first element fixedly connected in an axial direction to the catheter such that the first element is co-operable with a second element disposable on the radiation tube. A third element movably connects the first element and the second element, such as to be capable of causing a relative axial translation of the catheter relative to the radiation tube for manually positioning the radioactive source near the lesion, when the radiation tube is received within the catheter and the juncture is formed therebetween.

Further provided is a radiation tube for guiding a radioactive source into a catheter disposable in a blood vessel and to near a lesion of the blood vessel for treatment of the lesion. The radiation tube comprises an elongated radiation tube having a proximal end connectable to a drive device for driving a radioactive source through the radiation tube and a catheter to near a lesion of a blood vessel. The radiation tube has a distal portion receivable in the catheter lying outside of a blood vessel and the radiation tube. The radiation tube has on its distal portion a portion of an axial translation device. That portion comprises a second element fixedly connected in an axial direction to the radiation tube such that the second element is co-operable with a first element disposed on the catheter and a third element movably connecting the second element and first element such as to be capable of causing a relative axial translation of the catheter relative to the radiation tube for manually positioning the radiation source near the lesion, when the radiation tube is received within the catheter and the juncture is formed therebetween.

Lastly, there is provided an assembly of a radiation tube, a catheter and an axial translation device for placing a radioactive source near a lesion of a blood vessel for treatment of the lesion. The assembly comprises a catheter having at least one lumen and being extendible into a blood vessel such that a distal portion lies near a lesion and a proximal portion lies outside of the blood vessel. A radiation tube is provided for guiding a radioactive source through the radiation tube and the catheter to near the lesion. The radiation tube has a distal portion received in the lumen such that a juncture is formed between a proximal portion of the catheter and the radiation tube. An axial translation device is disposed at the juncture. The axial translation device comprises a first element fixedly connected in an axial direction to the catheter near the proximal portion, a second element fixedly connected in the axial direction to the radiation tube near the juncture, and a third element movably connected to the first element and the second element. Thus, by moving at least one of the elements a relative axial translation of the catheter and radiation tube is caused for manually positioning the radioactive source near the lesion.

DESCRIPTION OF PREFERRED EMBODIMENTS

Figure 1:
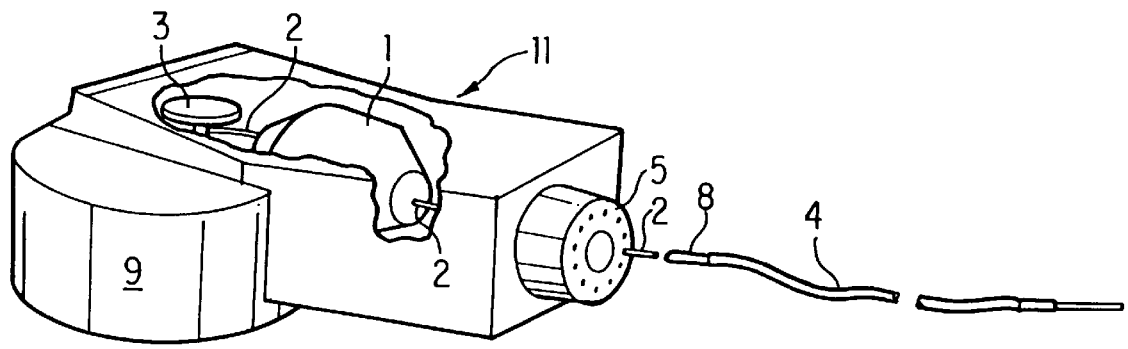
FIG. 1 is a diagrammatic illustration of the prior art afterloading machine, including the drive cable for the radioactive source and the radiation tube.

While the details of afterloading apparatus are described in the above-noted U.S. patents, the basic parts of a typical apparatus are shown in FIG. 1. A radioactive source (not shown in FIG. 1) is contained in a safe 1 which protects technicians from radiation while working with the apparatus. A source drive cable 2 is driven by a source drive mechanism 3 to position the radioactive source at the site of the therapy. A radiation tube 4 is disposed so as to guide the drive cable 2 to the site of the radioactive therapy. While not necessary for treating many lesion, the apparatus may also have a connection head 5 connecting one or more radiation tubes 4 to the drive cable. These connections are referred to as "channels". Only one radiation tube 4 and hence only one "channel" is shown in FIG. 1 for clarity and only one "channel" is necessary for treating many lesions. Generally, such apparatus also includes an adapter 8 for connecting the radiation tube 4 to the connection head 5. The multi-channeled connection head is common to many afterloading devices but is not necessary for the present invention. Thus, the connection head may have a single channel, e.g. a single channel in a central portion of the head.

While not shown in the drawings, such apparatus may also have a check cable, driven by a check cable drive. The check cable is used to test the connections of the apparatus to the patient prior to moving the radioactive source from the safe to the patient. Proper movement, back and forth, of a check cable with a "dummy" source attached to it ensures that all connections are operating properly and the radiation tube is correctly placed before the radioactive source is removed from the safe.

A drive means 9, such as a stepping motor, operates the drive mechanism 3 to move drive cable 2, with the source at a distal end thereof, from safe 1 through connection head 5, adapter 8 and radiation tube 4 to the site of the radiation therapy.

Figure 2:
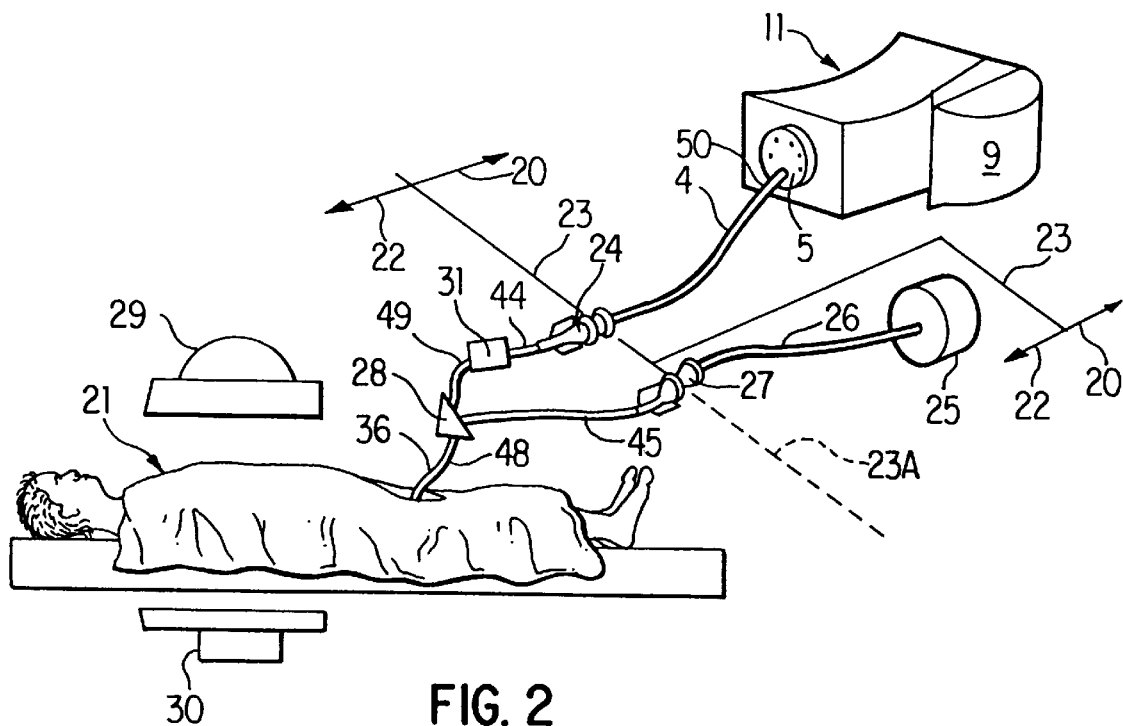
FIG. 2 is a diagrammatic illustration, in part showing prior art and in part showing the present apparatus arrangement for radiating a lesion.

FIG. 2 shows, in part, the prior art arrangement and, in part, the present invention for using the afterloading device of FIG. 1 for radiation of a lesion. In FIG. 2, the afterloading device, generally 11, is disposed in a non-sterile operating field indicated by arrows 20 while the patient, generally 21, is located in a sterile operating field, indicated by arrows 22. Thus, the sterile field and the non-sterile field are separated by demarcation 23 which is normally a wall.

The radiation tube 4 of the afterloader 11, which radiation tube is not sterile, connects to a coupling 24 which may be sterile and usually, but not necessarily, in the sterile operating field. A source of pressurized liquid 25 may connect through a duct 26 to a further coupling 27 to provide a source of pressurized liquid for inflating the balloons of a centering catheter, as described in more detail below, when a centering catheter is used. The source of pressurized liquid 25 and its connecting duct 26 may be in the sterile operating field, as shown, or in the non-sterile operating field, as shown by dashed line 23A. It is shown in the figure in the sterile operating field, as an example.

A Y-connection 28, described more fully below, connects the radiation tube 4 and source of pressurized fluid 25 for a cooperative operation, as again described more fully below. A radiation device 29, e.g. X-ray radiography or fluoroscopy device, cooperates with a receiver therefor 30 for imaging opaque materials in the body of the patient 21. In this particular case, that radiation device is used to exactly position the catheter and the source relative to the lesion.

While the subcutaneous insertion of the catheter and the radiation tube will depend upon the blood vessel being treated, the arrangement illustrated in FIG. 2 is a conventional arrangement for introduction thereof into a femoral artery of the leg and threaded therethrough to a coronary artery where angioplasty has taken place or is taking place.

As briefly described above, in order to correctly place the source at the lesion, in the prior art, the physician viewing the radiation displayed by receiver 30 communicated with a technician in the non-sterile field indicated by arrows 20 for operating the drive means 9, e.g. a stepping motor, to advance or withdraw the source, as required by the physician, to exactly place the source at the lesion. With the present invention, that difficulty and lack of precision of such placement is avoided by use of the present axial translation device 31, which is in the sterile operating field indicated by arrows 22 and operated by the physician in that sterile operating field as dictated by the physician's view of the receiver 30.

Figure 3:
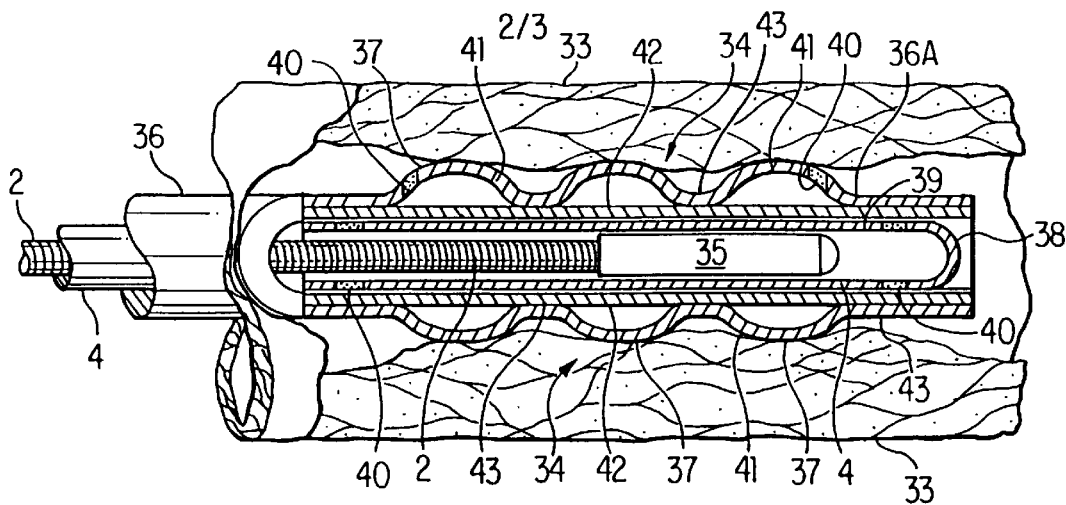
FIG. 3 shows the prior art arrangement of a centering catheter with balloons in a stenosis, a radiation tube within the lumen of the centering catheter, and a radioactive source (or "dummy") within the radiation tube.

FIG. 3 shows the arrangement of a centering catheter (if used), the radiation tube and source disposed within a lesion of the blood vessel. In the illustration of FIG. 3, the blood vessel 33 has a stenosis, generally 34 (but could be any lesion), which has been at least partially opened by angioplasty. After the angioplasty has been completed, the stenosis 34 is treated with radiation from a radioactive source 35 placed within the blood vessel 33 and near the stenosis 34. The centering catheter 36 (when used) is placed within the blood vessel with at least one centering balloon 37 (three shown in FIG. 3) thereof at least partially within the stenosis 34, i.e. a distal portion 36A lies near the lesion (stenosis) 34. A radiation tube 4 with a distal end 38 is placed within the centering catheter 36 such that at least a distal portion 39 thereof lies within the centering balloon(s) 37 for centering the distal portion 39 in the stenosis 34, with at least one of the centering balloon(s) 37 and the distal portion 39 usually having at least one readable marker 40 thereon. In the example shown in FIG. 3, the catheter 36 has an open end and the radiation tube 4 has a closed end. Other types of catheters have a closed end. In the latter case, the radiation tube does not have to be provided with a closed end. Further in this case, the radiation tube 4 may stop near axial translation device 31 (see FIG. 2) and be in longitudinal alignment with a closed end catheter 36. In such case, the source and the drive cable travel through the radiation tube 4 (up until the axial translation device 31) and then through a lumen of the catheter 36. Also, in the case of the open end radiation tube, the radiation tube need only enter the catheter lumen for a small distance, namely only the distance over which the radiation tube and the catheter may be moved relative to each other, as explained in detail below. In that case, the radioactive source moves from the afterloader machine through the radiation tube to a juncture between the radiation tube and the catheter and then through a lumen of the catheter from the juncture to the site of the lesion.

The source 35 is placed within the radiation tube 4 near the end portion 39 (or alternatively in the catheter, as explained above) such that the source 35 lies within the stenosis 34 and near at least one of the markers 40. The markers 40 are opaque to radiation, e.g. X-ray radiography and fluoroscopy devices, and, therefore, the physician can determine the position of the source 35 within the centering catheter 36 by viewing in receiver 30 the markers 40 and source 35 (see FIG. 2).

In the exemplary embodiment shown, the centering catheter 36 is provided with a plurality of inflatable centering balloons 37. These balloons are formed by an outer wall 41 connected to the catheter wall 42 with seals 43 to form the plurality of inflatable balloons 37. The seals 43 are made in a known manner.

The centering catheter 36 is placed within the stenosis 34, the radiation tube 4 is placed within the lumen of the centering catheter 36, and the radioactive source 35 is placed within the radiation tube 4 by excursion or retraction of drive cable 2. However, in the prior art, since the afterloader, generally 11 (see FIG. 2), is in a non-sterile operating field, the physician (in the sterile operating field) has to communicate with the technician operating the afterloader for appropriate movement of drive device 9 so as to position source 35 within the centering balloon 36. This causes the difficulties noted above. Also, as noted above, these difficulties are avoided by placing the present axial translation device 31 (see FIG. 2) in the sterile operating field so that the physician can view the position of source 35 within catheter 36 by means of the receiver 30 (see FIG. 2) and the physician can, preferably manually, operate the axial translation device 31, in the sterile operating field, for final adjustment and precise positioning of source 35 within the catheter 36, independently of the drive device 9 in the afterloader 11.

Figure 4:
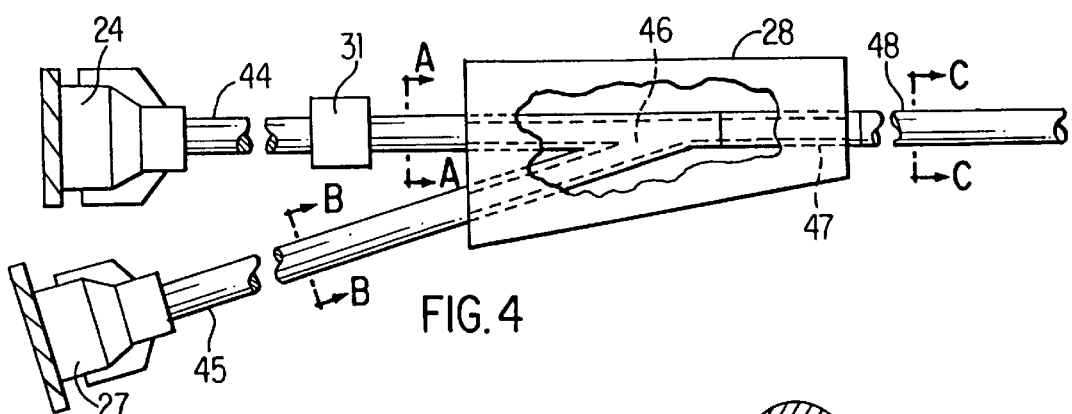
FIG. 4 shows more details of part of the arrangement of FIG. 2.
Figure 5:
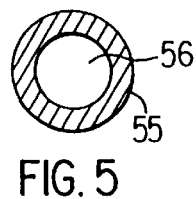
FIGS. 5 through 7 show lumens of tubes and catheter devices suitable for use with the present invention.
Figure 6:
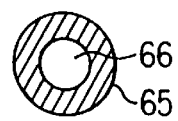
Figure 7:
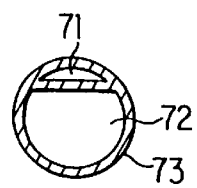

FIG. 4 shows more detail of the position of the present axial translation device 31 and a Y-connector 28. In FIG. 4, coupling 24 which couples radiation tube 4 (see FIG. 2) and coupling 27 which couples duct 26 (see FIG. 2) have respective extensions 44 of radiation tube 4 and 45 of duct 26 which form a Y connection 46 within Y-connector 28. Such Y-connectors generally have a strain relief section 47. Extensions 44 and 45 have generally concentric lumens, as shown in FIGS. 5 and 6. Thus, the extension walls 55 and 65 have a concentric lumen 56 and 66. However, common extension 48, as shown in FIG. 7, has a cross-section with separated lumens 71 and 72, surrounded by wall 73, which is common in the art. The foregoing describes extensions 44 and 45 with only one concentric lumen or two lumens. For purposes of understanding the present invention, it is not necessary and it would unduly burden the understanding where more lumens are shown. It should be understood, however, that multiple lumen catheters do exist and may be used with the present invention.

The axial translation device 31, which is disposed in the sterile field and may be operated by the physician in the sterile field, is disposed between Y-connector 28 and connector 24. Thus, the catheter 36 (which has at least one lumen 56, see FIG. 5) is placed in blood vessel 33 (see FIG. 3). The catheter has a distal portion 36A (see FIG. 3) near the lesion 34 and a proximal portion 49 (see FIG. 2) outside of the blood vessel 33. The radiation tube 4 (or its extension 44, see FIG. 2) is placed at least partially into catheter 36 (FIG. 3) through a lumen 56 such that a juncture 80 (see FIG. 8) is formed between the proximal portion 49 and the radiation tube 4. A proximal end 50 of radiation tube 4 (FIG. 2) is connected to drive device 9 through connection head 5 for driving the radiation source 35 (FIG. 3) through the radiation tube 4 (or its extension 44) and the catheter 36 to near lesion 34 (FIG. 3).

Figure 8:
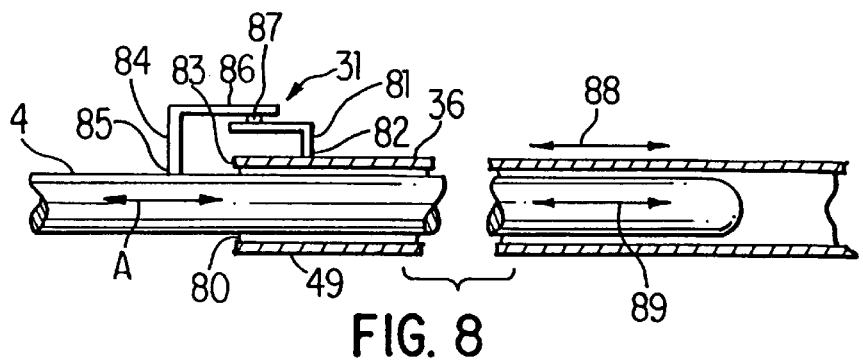
FIG. 8 is an overall diagrammatic illustration of the axial translation device of the present invention, as well as portions thereon assembled on a catheter and radiation tube and a combination of the so assembled catheter, radiation tube and translation device.

The axial translation device 31 (FIGS. 2, 4 and 8) is placed at the juncture 80 (FIG. 8). At least a portion of the axial translation device, e.g. a first element 81, is fixedly connected in the axial direction A to catheter 36 near the proximal portion 49. At least a portion of the axial translation device, e.g. a second element 84, is fixedly connected in the axial direction A to radiation tube 4 (or extension 44) near the juncture 80. The third element 86 is movably connected to the first element 81 and the second element 84. By moving one of elements 81, 84 and 86, a relative axial translation 88 of catheter 36 and radiation tube 4 is achieved, which will manually position the radiation source 35 (FIG. 3) near the lesion 34.

FIG. 8 shows a generalized concept of the present axial translation device. As shown in FIG. 8, the axial translation device 31 is at a juncture 80 of the catheter 36 and the radiation tube 4 (or its extension 44). There is a first element 81 which contacts the catheter 36 at contact point 82 near a proximal end 83 of catheter 36. A second element 84 contacts the radiation tube 4 at a position thereof near the proximal end 83 of the catheter 36 at contact point 85, i.e. contact point 85 is near juncture 80. Also, there is a third element 86 (which may be part of the element 84 or 81), and which contacts the first element 81 and the second element 84 at contact point 87. The first element 81 and second element 84 are connected to the catheter 36 and radiation tube 4, respectively, so as to be fixed, respectively, to each in an axial direction A of the catheter and radiation tube. Thus, by moving at least one of the elements 81, 84 and 86, a relative axial translation in axial direction A, shown by arrows 88 and 89, of the catheter 36 and the radiation tube 4 is achieved. The axial translation device 31 is arranged such that the axial translation is sufficient that the source 35 is accurately positioned within the lesion.

FIG. 8 is, of course, a very generalized diagrammatic illustration of the axial translation device of the present invention and is intended only to illustrate the principle involved and not specific mechanical embodiments thereof. However, as can be seen from FIG. 8, if one of elements 81, 84 and 86 is moved relative to one of the other elements, and since elements 81 and 84 contact the catheter 36 and the radiation tube 4 respectively, then, accordingly, the catheter 36 and the radiation tube 4 will be axially translated at juncture 80, which will cause the relative position of radiation tube 4 together with source 35 therein and the catheter 36 to be adjusted, either forward or reverse, as depicted in FIG. 8 (due to both of them being fixed relative to each other because of both of them being fixedly connected to the afterloader machine). Thus, while the technician can approximately position source 35 with the drive device 9 within the catheter 36 as guided by markers 40, when present, and related by the physician viewing in receiver 30, for final and precise positioning of radiation tube 4 relative to catheter 36 and hence the position of source 35, the physician in the sterile operating field may operate the axial translation device, illustrated in FIG. 8, independently of the drive device 9 to very precisely position source 35 within the lesion 34 for equal radiation treatment of the lesion.

As is common in the art, the radioactive source may either be a gamma-ray source or a beta-ray source.

Elements 81, 84 and 86 may be chosen from a wide variety of mechanical elements to achieve such axial translation. The elements may be, among others, a lever, wheel, screw thread or gear thread and made of a variety of materials, e.g. metals and plastics, for example.

Figure 9:
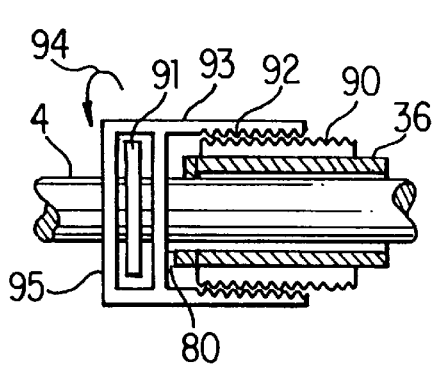
FIGS. 9 through 12 show specific embodiments of the axial translation device of the present invention.

FIG. 9 illustrates a screw thread for the elements where a screw thread 90 is contacted (attached) in the axial direction A to catheter 36. A positive stop 91 contacts (is attached) in the axial direction A to radiation tube 4 in a fixed relationship as the second element. A cooperative screw thread 92 is disposed on arm 93 such that revolving arm 93 by the physician, as indicated by arrow 94, causes rotation of arm 93 and moves positive stop 91 forward or backward in relationship to juncture 80 of catheter 36 and radiation tube 4. This forward and reverse motion is achievable by annular ring 95 moving positive stop 91 backward or forward.

Figure 10:
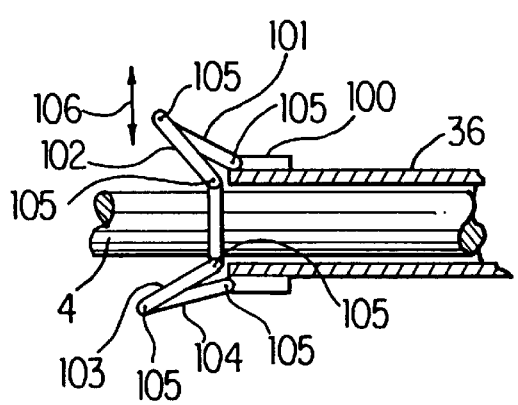

FIG. 10 illustrates the axial translation device in the form of a combination of levers connected by pivot axles. In this embodiment, a contactor 100 contacts (is attached to), in axial direction A, a catheter 36. A combination of levers 101, 102, 103 and 104 have pivot axles 105 which cause translation of catheter 36 relative to radiation tube 4 when the levers are depressed or expanded as indicated by arrow 106.

Figure 11:
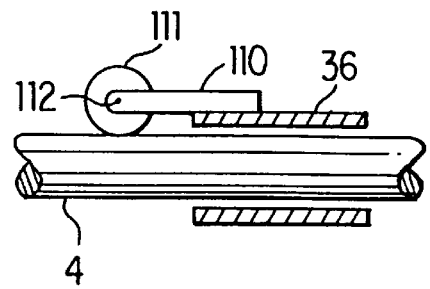

FIG. 11 illustrates an embodiment where the axial translation device is a wheel rotatably affixed to an arm by an axle. In this embodiment, an arm 110 contacts (is attached to), in axial direction A, catheter 36, as the first element. A wheel 111 frictionally contacts radiation tube 4, as the second element. Wheel 111 may be rotationally fixed in one of a number of known ways, e.g. a pin-in-hole construction. An axle 112 allows the wheel to be rotatably affixed to the arm and functions as the third element. In this embodiment, by the physician, in the sterile operating field, rotating wheel 111, a similar translation of catheter 36 and radiation tube 4 occurs.

Figure 12:
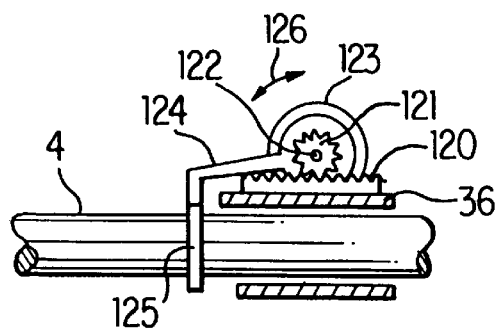

FIG. 12 shows the use of a wheel and gear threads, particularly in the form of a rack and pinion as the axial translation device. In that embodiment, a rack 120 contacts (is attached to), in axial direction A, catheter 36 and cooperates with a pinion 121, movable via axle 122, by way of thumb wheel 123. A connecting arm 124 contacts radiation tube 4 by way of connecting ring 125, i.e. connecting ring 125 is fixedly connected to radiation tube 4 in the axial direction A. Therefore, by rotating thumb wheel 123, as shown by arrow 126, the rack and pinion arrangement translates catheter 36 and radiation tube 4 in a similar manner. Pinion 121 may be rotationally fixed in one of a number of known ways, e.g. by a pin-in-hole construction.

Of course, a wide variety of mechanical devices may be used to achieve the translation, and the above is merely to illustrate that variety. The important point is not the specific mechanical arrangements to achieve that translation, but the placing of the axial translation device at the juncture of the catheter and radiation tube such that the first element contacts the catheter near a proximal end thereof, the second element contacts the radiation tube at a position thereof near the proximal end of the catheter, i.e. near the juncture, and the third element contacts the first element and the second element such as to provide axial translation between the first element and the second element so as to cause a relative axial translation of the catheter and radiation tube sufficient that the source is positioned within the lesion. It is further important that this translation device be in the sterile field, so that it can be manipulated by the physician in that sterile operating field.

For purposes of providing the invention in convenient form for use by a physician in the sterile field, as a first embodiment, a portion of the translation device 31 may be disposed on radiation tube 4, or its extension 44 and, as a second embodiment, a portion of the translation device 31 may be disposed on catheter 36, as shown particularly in FIGS. 9 and 12. As a third embodiment, the radiation tube, catheter and axial translation device may be provided as an assembled unit, particularly as shown in FIG. 10.

In regard to the first of these embodiments, the invention provides a radiation tube for guiding a radioactive source into a catheter disposable in a blood vessel and to near a lesion of the blood vessel for treatment of the lesion. The radiation tube comprises an elongated radiation tube 4 having a proximal end 50 connectable to a drive device 9 for driving a radioactive source 35 through the radiation tube 4 and a catheter 36 to near a lesion of a blood vessel 33. The radiation tube 4 has a distal portion 36A receivable in the catheter 36 lying outside of a blood vessel 33 and the radiation tube 4. The radiation tube 4 has on its distal portion 36A and near juncture 80 a portion of an axial translation device 31. That portion comprises a second element 84 fixedly connected in an axial direction A to the radiation tube 4 such that the second element 84 is co-operable with a first element 81 disposable on the catheter 36 and the third element 86 movably connectable to the second element 84 and first element 81 such as to be capable of causing a relative axial translation 88 of the catheter 36 relative to the radiation tube 4. This allows manually positioning the radiation source 35 near the lesion 34, when the radiation tube is received within catheter 36 and the juncture 80 is formed therebetween.

In regard to the second of these embodiments, the invention provides a catheter for guiding a radioactive source near a lesion of a blood vessel for treatment of the lesion, comprising an elongated catheter 36 having at least one lumen 56 and being extendible into a blood vessel 33 such that a distal portion 36A lies near a lesion 34 and a proximal portion 49 lies outside of the blood vessel 33. The lumen 56 is capable of at least partially receiving a radiation tube 4 for transporting a radioactive source 35, such that a juncture 80 is formable between the proximal portion 49 of the catheter 36 and the radiation tube 4. The catheter has on the proximal portion 49 a portion of an axial translation device 31. That portion comprises a first element 81 fixedly connected in an axial direction A to the catheter 36 such that the first element 81 is co-operable with a second element 74 disposable on the radiation tube 4 and a third element 86 movably connectable to the first element 81 and the second element 84 such as to be capable of causing a relative axial translation 88 of the catheter 36 relative to the radiation tube 4. This allows manual positioning the radioactive source 35 near the lesion 34, when the radiation tube 4 is received within the catheter 36 and a juncture 80 is formed therebetween.

In regard to the third of these embodiments, the invention provides an assembly of a radiation tube, a catheter and an axial translation device for placing a radioactive source near a lesion of a blood vessel for treatment of the lesion. The assembly comprises a catheter 36 having at least one lumen 56 and being extendible into a blood vessel 33 such that a distal portion 36A lies near a lesion 34 and a proximal portion 49 lies outside of the blood vessel 33. A radiation tube 4 is provided for guiding a radioactive source 35 through the radiation tube 4 and the catheter 36 to near the lesion 34. The radiation tube 4 has a distal portion 36A received in the lumen 56 such that a juncture 80 is formed between a proximal portion 49 of the catheter 36 and the radiation tube 4. An axial translation device 31 is disposed at the juncture 80. The axial translation device 31 comprises a first element 81 fixedly connected in an axial direction A to the catheter 36 near the proximal portion 49, a second element 84 fixedly connected in the axial direction A to the radiation tube 4 near juncture 80, and a third element 86 movably connected to the first element 81 and second element 84, such that moving at least one of the elements (81, 84 and 86) causes a relative axial translation 88 of the catheter 36 and radiation tube 4. This allows manually positioning the radioactive source 35 near the lesion 34.

It is apparent that the invention is amenable to various modifications within the scope and spirit of the disclosure, and it is intended that those modifications be embraced by the annexed claims.

What is claimed is:

1. A method of treating a lesion (34) of a blood vessel (33) with radiation from a radioactive source (35), comprising:
   1) placing a catheter (36) having at least one lumen (56) into the blood vessel (33) with a distal portion (36A) near the lesion (34) and a proximal portion (49) outside of the blood vessel (33);
   2) placing a radiation tube (4) at least partially into the catheter (36) through the lumen (56) thereof such that a juncture (80) is formed between the proximal portion (49) of the catheter (36) and the radiation tube (4);
   3) connecting a proximal end of the radiation tube (4) to a drive device (9) for driving the radioactive source (35) through the radiation tube (4) and the catheter (36) near the lesion (34);
   4) placing an axial translation device (31) at the juncture (80), said axial translation device (31) comprising a first element (81) fixedly connected in an axial direction (A) to the catheter (36) near the proximal portion (49) thereof, a second element (84) fixedly connected in an axial direction (A) to the radiation tube (4) near the juncture (80), and a third element (86) movably connected to the first element (81) and the second element (84); and
   5) manually moving at least one of the elements (81, 84 and 86) so as to cause a relative axial translation (88) of the catheter (36) and radiation tube (4) for manually positioning the radioactive source (35) near the lesion (34).

2. The method of claim 1, wherein the elements are sterile and are disposed and operated in a sterile operating field.

3. The method of claim 1, wherein a marker (40) on the catheter (36) and the source (35) are opaque to radiation and the moving of the at least one element is performed while viewing positions of the marker and the source under a radiation device (29, 30).

4. The method of claim 3, wherein the radiation device is a fluoroscopy device (29, 30).

5. The method of claim 1, wherein the radioactive source (35) is a gamma-ray source or a beta-ray source.

6. The method of claim 1, wherein a centering balloon (37) having a plurality of inflatable segments is disposed on the distal portion of the catheter.

7. The method of claim 1, wherein the blood vessel (33) is a coronary blood vessel.

8. The method of claim 7, wherein the treatment is in conjunction with a percutaneous translumenal coronary angioplasty.

9. The method of claim 8, wherein the treatment is sufficient to at least retard restenosis of the angioplasty.

10. The method of claim 1, wherein at least one of the elements is a lever, wheel, screw thread and gear thread.

11. The method of claim 10, wherein at least one of the elements is a wheel.

12. The method of claim 10, wherein at least one of the elements is a gear thread.

13. The method of claim 1, wherein the axial translation device (31) is a rack (120) and pinion (121).

14. The method of claim 1, wherein the axial translation device (31) is a wheel (111) rotatably affixed to an arm (110) by an axle (112).

15. The method of claim 1, wherein the axial translation device (31) is cooperative screw threads (90, 92) for moving a positive stop (91).

16. The method of claim 1, wherein the axial translation device (31) is a combination of levers (101–104) connected by pivot axles (105).

17. An apparatus for treating a lesion (34) of a blood vessel (33) with radiation from a radioactive source (35), comprising:

1) a catheter (36) having at least one lumen (56) with a distal portion (36A) disposable within the blood vessel (33) near the lesion (34) and a proximal portion (49) disposable outside of the blood vessel (33);

2) a radiation tube (4) at least partially disposed into the catheter (36) through the lumen (56) whereby a juncture (80) is formed between the proximal portion (49) of the catheter (36) and the radiation tube (4);

3) a connection for connecting a proximal end of the radiation tube (4) to a drive device (9) for driving the radioactive source (35) through the radiation tube (4) and into the catheter (36) near the lesion (34);

4) an axial translation device (31) disposed at the juncture (80), said axial translation device (31) comprising a first element (81) fixedly connected in an axial direction (A) to the catheter (36) near the proximal portion (49) thereof, a second element (84) fixedly connected in the axial direction to the radiation tube (4) near the juncture (80), and a third element (86) movably connected to the first element (81) and the second element (84);

and wherein manually moving at least one of the elements (81, 84 and 86) causes a relative axial translation (88) of catheter (36) and radiation tube (4) for manually positioning the radioactive source (35) near the lesion (34).

18. The apparatus of claim 17, wherein the elements are sterile for disposition and operation in a sterile operating field (22).

19. The apparatus of claim 17, wherein a marker (40) on the catheter (36) is opaque and the source (35) is opaque to radiation and positions of the marker (40) and source (35) are viewable under a radiation device (29, 30).

20. The apparatus of claim 19, wherein the radiation device is a fluoroscopy device (29, 30).

21. The apparatus of claim 17, wherein the radioactive source (35) is a gamma-ray or a beta-ray source.

22. The apparatus of claim 17, wherein a centering balloon (37) having a plurality of inflatable segments is disposed on a distal portion of the catheter.

23. The apparatus of claim 17, wherein the radioactive source (35) is capable of inducing an amount of radiation for at least retarding restenosis of the angioplasty.

24. The apparatus of claim 17, wherein at least one of the elements is a lever, wheel, screw thread and gear thread.

25. The apparatus of claim 24, wherein at least one of the elements is a wheel or gear thread.

26. The apparatus of claim 17, wherein the axial translation device (31) is a rack (120) and pinion (121).

27. The apparatus of claim 17, wherein the axial translation device (31) is a wheel (111) rotatably affixed to an arm (110) by an axle (112).

28. The apparatus of claim 17, wherein the axial translation device (31) is cooperative screw threads (90, 92) for moving a positive stop (91).

29. The apparatus of claim 17, wherein the axial translation device (31) is a combination of levers (101–104) connected by pivot axles (105).

30. A catheter for guiding a radioactive source near a lesion of a blood vessel for treatment of the lesion, comprising an elongated catheter (36) having at least one lumen (56) and being extendible into a blood vessel (33) such that a distal portion (36A) lies near a lesion (34) and a proximal portion (49) lies outside of the blood vessel (33), said lumen (56) having at least partially received therein a radiation tube (4) for transporting a radioactive source (35), such that a juncture (80) is formed between the proximal portion (49) of the catheter (36) and the radiation tube (4), said catheter having on the proximal portion (49) a portion of an axial translation device (31), said portion comprising a first element (81) fixedly connected in an axial direction (A) to the catheter (36) such that the first element (81) cooperates with a second element (84) disposed on the radiation tube (4) and a third element (86) is movably connected to the first element (81) and the second element (84), wherein a relative axial translation (88) of the catheter (36) relative to the radiation tube (4) is provided for manually positioning the radioactive source (35) near the lesion (34).

31. A radiation tube for guiding a radioactive source into a catheter disposable in a blood vessel and to near a lesion of the blood vessel for treatment of the lesion, comprising an elongated radiation tube (4) having a proximal end (5) connectable to a drive device (9) for driving a radioactive source (35) through the radiation tube (4) and catheter (36) to near the lesion (34) of the blood vessel (33), said radiation tube (4) having a distal portion (36A) received in the catheter (36) such that a juncture (80) is formed between a proximal portion (49) of the catheter (36) lying outside of the blood vessel (33) and the radiation tube (4), said catheter (36) having on the proximal portion (49) a first element (81) of an axial translation device (31), said radiation tube (4) having on its distal portion (36A) and near juncture (80) a second element (84) of the axial translation device (31) fixedly connected in an axial direction (A) to the radiation tube (4), said first element (81) and said second element (84) co-operate with a third element (86) movably connected to the first element (81) and second element (84) whereby relative axial translation (88) of the catheter (36) relative to the radiation tube (4) is provided for manually positioning the radioactive source (35) near the lesion (34).

32. An assembly of a radiation tube, a catheter and an axial translation device for placing a radioactive source near a lesion of a blood vessel for treatment of the lesion, comprising:

(1) a catheter (36) having at least one lumen (56) and being extendible into a blood vessel (33) such that a distal portion (36A) lies near a lesion (34) and a proximal portion (49) lies outside of the blood vessel (33);

(2) a radiation tube (4) for guiding a radioactive source (35) through the radiation tube (4) and the catheter (36) to near the lesion (34), said radiation tube (4) having a distal portion (36A) received in the lumen (56) such that a juncture (80) is formed between a proximal portion (49) of the catheter (36) and the radiation tube (4);

(3) an axial translation device (31) disposed at the juncture (80), said axial translation device (31) comprising a first element (81) fixedly connected in an axial direction (A) to the catheter (36) near the proximal portion (49), a second element (84) fixedly connected in the axial direction (A) to the radiation tube (4) near juncture (80), and a third element (86) movably connected to the first element (81) and second element (84), whereby moving at least one of the elements (81, 84 and 86) causes a relative axial translation (88) of the catheter (36) and radiation tube (4) for manually positioning the radioactive source (35) near the lesion (34).

* * * * *